United States Patent [19]

Kulig

[11] Patent Number: 4,695,705
[45] Date of Patent: Sep. 22, 1987

[54] APPARATUS AND METHOD FOR LOCALIZED HEATING OF AN OBJECT AT PRECISE TEMPERATURES

[75] Inventor: Frank M. Kulig, Bloomfield, Conn.

[73] Assignee: The J. M. Ney Company, Bloomfield, Conn.

[21] Appl. No.: 829,838

[22] Filed: Feb. 14, 1986

[51] Int. Cl.⁴ .......................... F24H 3/00; B23Q 1/04
[52] U.S. Cl. ................................ 219/354; 219/85 BA; 219/85 BM; 219/347; 219/349; 219/358; 219/405; 219/411; 269/71; 269/73
[58] Field of Search ............ 219/85 BA, 85 BM, 347, 219/349, 354, 358, 405, 411; 269/71, 73

[56] References Cited

U.S. PATENT DOCUMENTS

| | | | |
|---|---|---|---|
| 2,110,632 | 3/1938 | Mitchell | 219/8 |
| 3,592,992 | 7/1971 | Costello | 219/349 |
| 3,661,369 | 5/1972 | Costello | 219/349 X |
| 3,710,069 | 1/1973 | Papadopoulos et al. | 219/85 |
| 3,712,984 | 3/1971 | Lienhard | 250/86 |
| 3,764,772 | 10/1973 | Matsuchek | 219/85 |
| 3,812,318 | 5/1974 | Yoshizumi et al. | 219/85 |
| 4,233,493 | 11/1980 | Nath | 219/354 |
| 4,298,806 | 11/1981 | Herold | 250/504 H |
| 4,412,134 | 10/1983 | Herold et al. | 250/504 R |
| 4,421,987 | 12/1983 | Herold | 250/492.1 |
| 4,505,464 | 3/1985 | Chitayat | 269/73 |
| 4,538,070 | 8/1985 | Herold et al. | 250/504 R |
| 4,546,261 | 10/1985 | Gonser et al. | 250/492.1 |

Primary Examiner—E. A. Goldberg
Assistant Examiner—Gerald Preston

[57] ABSTRACT

Apparatus for and a method of precisely positioning an object to be subjected to localized heating at precise temperatures at the second focal point of an elliptical reflector which has an infra-red source at its first focal point. The apparatus includes a platform to support the workpiece for vertical movement relative to the reflector and infra-red source, and a movable probe which has a free end positionable in the axis of the reflector and in the plane of its second focal point to guide movement of the platform and workpiece to the second focal point.

6 Claims, 5 Drawing Figures

APPARATUS AND METHOD FOR LOCALIZED HEATING OF AN OBJECT AT PRECISE TEMPERATURES

FIELD OF THE INVENTION

This invention relates to a method and apparatus for localized heating of a workpiece at precise temperatures and, more particularly, relates to such a method and apparatus utilizing infra-red energy and especially adapted to dental laboratory usage.

BACKGROUND OF THE INVENTION

Techniques of heating an object for soldering using concentrated infra-red energy are disclosed in the prior art, as exemplified by U.S. Pat. Nos. 3,592,992 and 3,710,069. In these known systems, a source of infra-red light is placed at a first focal point within an elliptical reflector, and the light emitted from the source is reflected to a second focal point and utilized to heat or otherwise work on an object.

In many applications, it is desired that the reflected infra-red energy be focused at a point. This cannot be completely achieved unless the infra-red light source is a point source, which is essentially impossible in view of available infra-red sources. Therefore, it is desired to have the workpiece to be acted upon at, or essentially at, the second focal point to minimize the area of heating and to concentrate the reflected energy in this area. If the workpiece is axially spaced to either side of the second focal point, the area which is heated will be greater, and the reflected energy less per unit area. However, with the workpiece precisely positioned in the plane of the second focal point, the workpiece may be subjected to maximum heat in a small controlled area for a limited period of time so that heat transfer to adjacent area is minimized.

In some applications, the control of heat on the workpiece to be soldered or heated can be quite critical. For example, in the fabrication of dental bridges with crowns, the time of application of high heat can be quite critical. The present practice of soldering crowns together to form a bridge involves the use of gas torches which produce a flame of 4400°–5000° F. depending upon the type of gas being combusted. The crowns are generally cast from alloys which have a melting point of less than 2200° F. Thus, to melt a flux on the surfaces of the crowns to be soldered, and then to liquify a solder perform between the crowns to produce bonding thereof, is a very precise operation which requires much skill in conducting the point of application of heat and the time the source heat is applied.

The present invention overcomes these problems by providing a new and improved apparatus and method for localizing heat and controlling the temperature and time of application of the heat energy so as not to damage a workpiece which is being processed.

SUMMARY OF THE INVENTION

Briefly stated, the invention in one form as embodied in an apparatus comprises a housing member which supports an electrically energizable infra-red source within an elliptical reflector at a first focal point within the reflector. The reflector is symmetrical about a longitudinal axis. Mounted upon the housing is a pivotal arm carrying a vertically depending probe having a free end which resides in a plane which essentially contains the second focal point of the elliptical reflector. The arm is pivotal about an axis remote from the axis of the reflector to move the probe to an operative position where the free end thereof is coaxial with the axis of the reflector, and to a retracted position where the probe is outside of the reflected infra-red energy.

A platform is vertically movable relative to the housing beneath the reflector and is adapted to support a workpiece to be heated or soldered. The workpiece to be heated is placed on the platform, or on a carrier on the platform. The arm is then pivoted to bring the free end of the probe to a position coaxial with the axis of the reflector, and then the platform and the associated workpiece are moved to position the workpiece beneath and essentially at the free end of the probe. Thereafter, the probe is pivoted to its retracted or inoperative position, and the operator then eneregizes the infra-red source to heat the workpiece.

The invention is particularly useful in dental applications. For example, in the making of bridges, it is necessary to solder two or more alloy crowns together without melting or stressing the material of the crowns. The production of dental crowns is greatly facilitated by first applying the flux; then the alloy of the crown is heated with the infra-red energy to a temperature less than the melting point of the crown alloy, but to a temperature sufficient to cause the flux to flow and cleanse the adjoining surfaces to be soldered together. The flux is transparent or insensitive to the infra-red radiation and merely reacts to the temperature of the crown. The crown is heated, thus heating the flux by conduction to produce the necessary meeting of the flux and cleansing of the surfaces to be soldered. Thereafter, a solder perform is placed between the crown castings and melted with the infra-red energy at a temperature which is insufficient to melt the crown alloy, but sufficient to melt the solder and bond the two crowns into a bridge.

The invention is also very useful in reglazing the porcelain on a crown which has been ground to fit the bite of a patient, either by remelting a surface portion of the porcelain coating, or by applying and firing an additional porcelain deposit on the surface area to be reglazed.

The invention further provides means for controlling the level of energization of the infra-red source and therefore controlling the temperature at the second focal point.

An object of this invention is to provide a new and improved method and apparatus for heating a localized area of a workpiece with precise temperature control using infra-red energy.

Another object of this invention is to provide a method for heating a workpiece with infra-red energy using new and improved means for precisely controlling the temperature at the point on the workpiece to be heated.

A further object of this invention is to provide a new and improved method for joining dental crowns to form a dental bridge.

The features of the invention which are believed to be novel are particularly pointed out and distinctly claimed in the concluding portion of the specification. The invention, however, together with further objects and advantages thereof, may best be appreciated by reference to the following detailed description taken in conjunction with the attached drawings.

DETAILED DESCRIPTION OF PREFERRED EMBODIMENT OF THE INVENTION

Figure 1:
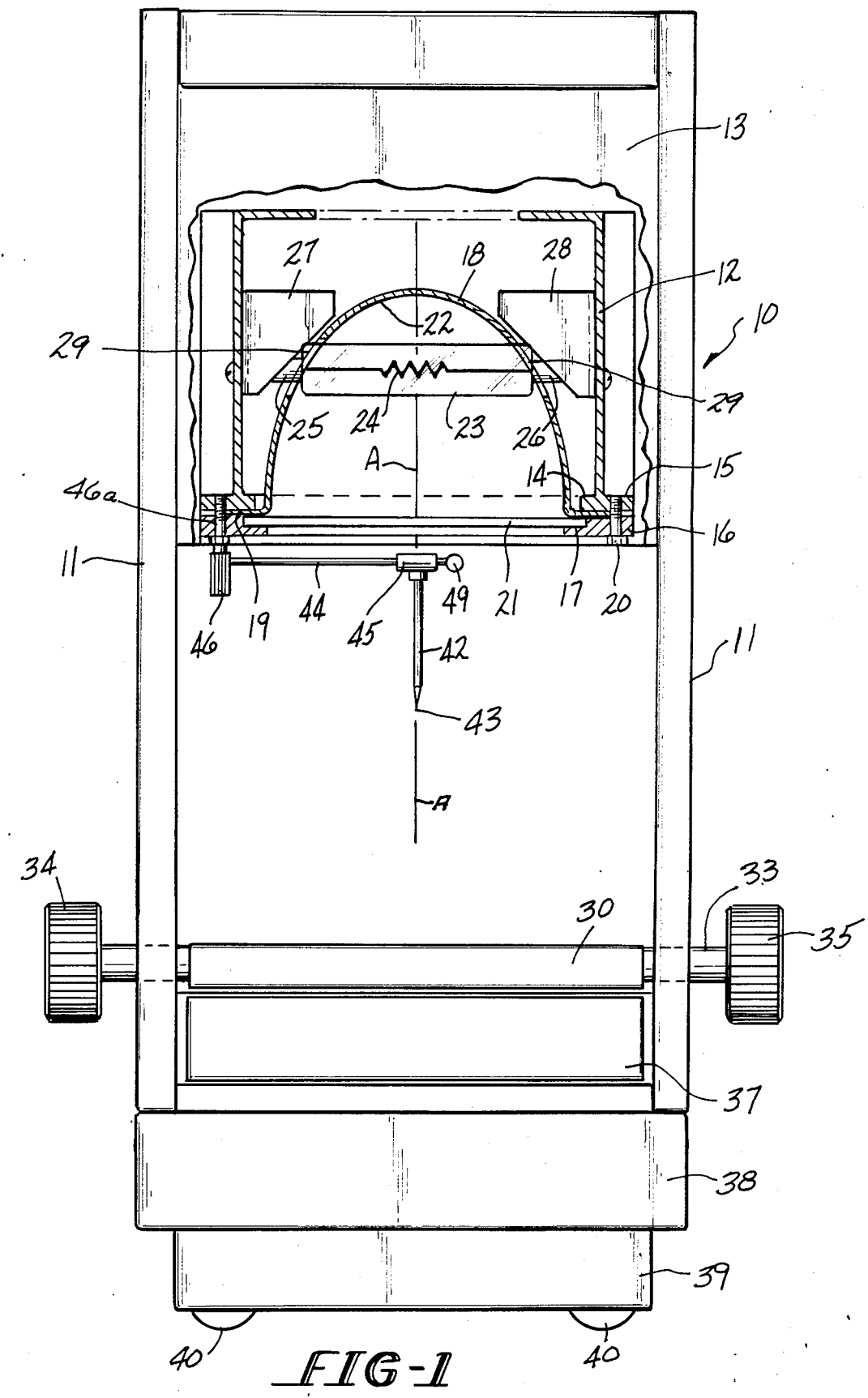
FIG. 1 is a front elevational view of an apparatus embodying the invention with a portion thereof partially broken away.
Figure 2:
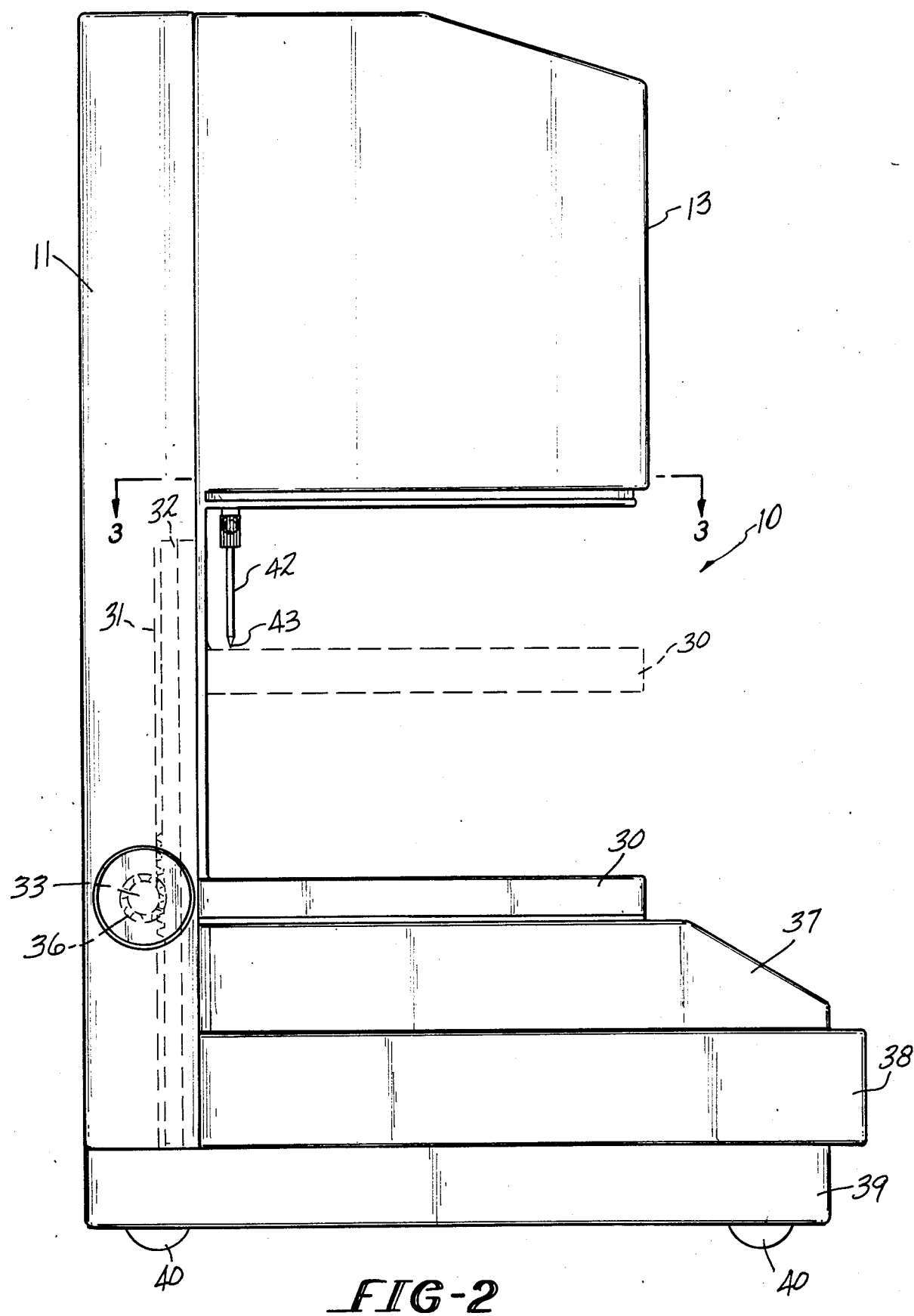
FIG. 2 is a side elevational view seen from the left side of the apparatus of FIG. 1.
Figure 3:
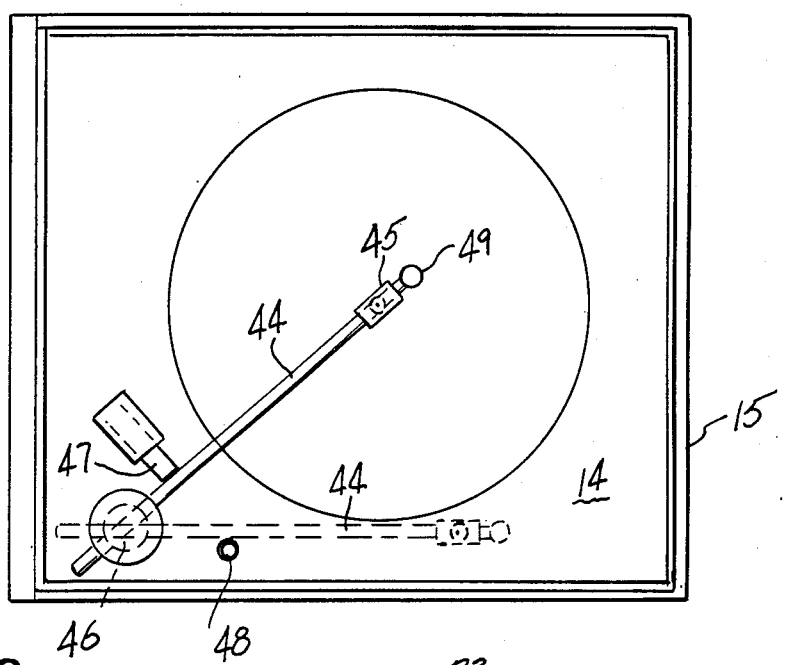
FIG. 3 is a sectional view along the line 3—3 in FIG. 2.

Turning now in detail to FIGS. 1-3, an apparatus embodying the invention comprises a support assembly 10 with two upright support members 11, and a housing 12 supported thereon. The housing member 12 is normally concealed behind the front panel 13 which is supported upon the support frame or assembly 10. The housing 12 is supported within the support frame 10 by fasteners (not shown) extending from on the support members 11, and it has an inwardly extending peripheral annular flange 14 and an outwardly extending rectangular flange 15. Disposed below flanges 14 and 15 is a securing member 16 having a shoulder 17. The elliptical reflector 18 has an annular circumferential flange 19 which is received between the flange 14 of the housing 12 and the securing member 16 which, in turn, is secured to the housing 12 by means of bolts 20 or other suitable fastening means. Supported on the shoulder 17 is an annualar quartz member 21 to seal and protect the reflective surface 22 of the reflector 18.

Disposed at a first focal point within the elliptical reflector 18 is an infra-red lamp 23. It will be noted that the lamp cannot be considered a point source in view of the length of its coil 24 which extends to terminals 25 and 26 that are electrically connected to supporting members 27 and 28, respectively, secured to housing member 12. Thus, the reflector 18 and infra-red lamp 23 are fixed in position within the housing 12 which is in a fixed position upon the vertical supports 11. Apertures 29 and 29a are defined in the reflector 18 to permit the terminals of lamp 23 to extend to the supports 27 and 28.

In a typical application, lamp 23 is a 1000 watt tungsten quartz-iodine lamp. The reflecting surface 22 of reflector 18 is provided by bright gold electroplate over a very smooth surface to minimize absorption of infra-red rays.

Reference is now made to FIG. 2 in conjunction with FIG. 1. A vertically movable platform 30 is connected to a rack 31 which is vertically movable on a guide 32 affixed to a wall extending between the support members 11. A shaft 33 having thumbwheels 34 and 35 at either end thereof carries a pinion 36 in engagement with the rack 31, and the shaft 33 is journalled in support members 11. Platform 30 may be moved in the vertical direction by manipulation of the thumbwheels 34 or 35.

The apparatus further includes a compartment element 37 which may house electrical circuitry hereinafter described, and also provides space for a drawer 38. The support members 11 may extend to a base member 39 which rests on the feet 40.

It will be noted from FIG. 1 that a probe member 42 having a free end 43 vertically depends from the horizontal arm 44. Probe member 42 includes a sleeve 45 for mounting on the arm 44, and the position thereon may be adjusted.

Reference is now made to FIG. 3 in conjunction with FIGS. 1 and 2. The arm 44 is seated in a knob 46 which is rotatable on the shaft 46a so that it may be pivoted to a position shown in FIG. 1 where the axis of the probe member 42 coincides with the axis A of the reflector. In this position, the arm 44 engages a stop 47 on the flange 14 of the housing 12. The reflector 18 is omitted in FIG. 3

As shown in FIG. 3, the arm 44 is pivotable between the full line position shown which corresponds to the position shown in FIG. 1, and the dotted line position shown in FIG. 3 where it rests against a pin stop 48 seated in the flange 15. A finger grip 49 is provided at the end of the arm 44. The free end 43 of the probe member 42 is in a horizontal plane which includes the second focal point of the reflector 18.

When a workpiece is to be soldered, it is preferably placed on a thermal insulating block B (FIG. 5) on the platform 30. Then the platform 30 is raised to bring the area to be soldered to the free end 43 of the probe member 42, which is then pivoted to its inoperative position. The infra-red lamp 23 is energized and infra-red energy is reflected to the second focal point F2.

A three-sided darkened transparent shield (not shown) may be disposed about the housing 12 and is pulled down to enclose the working area on the platform 30.

Figure 4:
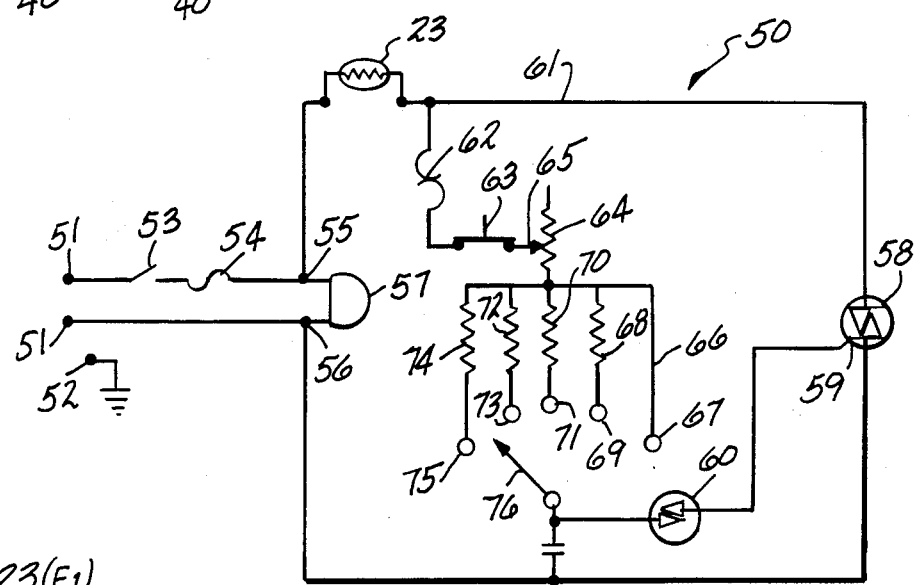
FIG. 4 is an electrical schematic diagram of the controls for the apparatus of FIG. 1.

Reference is now made to FIG. 4, which exemplifies the electrical control for the infra-red bulb 23. A circuit 50 is provided which comprises a plug to a 120 volt outlet with two terminals 51, and a conventional ground terminal 52. An "On/Off" switch 53 is provided in a circuit with a fuse 54 leading to the terminals 55 and 56. A pilot lamp 57 is connected across the terminals 55 and 56 to indicate that the device is "On" or "Off". Terminal 55 is connected directly to bulb 23 which has in series therewith a triac 58. A gate 59 of the triac 58 is controlled by as asymmetrical switch 60 which will determine the On/Off time of the triac and the resultant time of the sixty cycle sine wave which passes the triac in both directions.

Coupled to the line 61 in which the infra-red lamp 22 resides is a circuit leading to the gate 59 of the triac 58, and it comprises a thermal overload switch 62, an operator's foot switch 63, a potentiometer 64 having an arm 65, and a circuit comprising five power level selectors. The power level selectors comprise a direct circuit 66 to the switch contact 67, a resistance 68 to the contact 69, a resistance 70 to the contact 71, a resistance 72 to the contact 73, and a resistance 74 to the contact 75. The terminals 67, 69, 71, 73 and 75 are arranged to be contacted by a switch selector arm 76 to determine the power level applied to the infra-red lamp. The resistances 68, 70, 72 and 74 are so selected that if the switch arm 76 is at contact 67 and provides one hundred percent power, then contact 69 will provide eighty percent power, contact 71 will provide sixty percent power, contact 74 will provide forty percent power, and contact 75 will provide twenty percent power. The potentiometer 64 provides for graduations of twenty percent within the power levels. These power levels will ultimately determine the temperature which can be generated at a workpiece.

For example, a workpiece 0.5"×0.5"×0.020" could reach a temperature of 3000° Fahrenheit throughout its mass in approximately one minute at full power if the switch arm were connected to terminal 67 and the infra-red lamp source provided 1000 watts at 120 volts. If the workpiece were larger, the time in reaching a given temperature, as exemplified in the previous stated example of 3000° Fahrenheit, would be longer. Then the amount of heat in the same one minute of time for the specified size workpiece would be in the ratios of twenty, forty, sixty and eighty percent for the switch terminals 75, 73, 71 and 69, respectively. Thus, the invention provides an upper limit with respect to time at which heating will occur at the second focal point $F^2$ (See FIG. 5).

As previously mentioned, the apparatus and method disclosed are particularly useful in dental applications. Consider, for example, the joining of a pair of dental crowns to form a two unit bridge, and assume that the crowns are made of an alloy which is identified by the trademark OPTION of The J. M. Ney Company of Bloomfield, Conn. This alloy consists predominantly of palladium, copper and gallium, with small percentages of gold and boron, as disclosed in U.S. Pat. No. 4,387,072 assigned to The J. M. Ney Company. Such an alloy has a melting point of about 2150° Fahrenheit.

In providing a solder connection between two crowns to form a bridge, the crowns are spaced closely together, generally on the order of 0.5 millimeter. Then a flux is introduced between the surfaces to be soldered. The purpose of the flux, which with the alloy specified, will probably be a fluoride flux, is to flow and cleanse the surfaces to which the solder is desired to adhere. The flux reduces oxides on these surfaces and provides a function similar to pickling with an acid to cleanse any metallic oxides and make the surfaces wettable. The flux itself is transparent to the infra-red energy.

The infra-red energy heats the crowns to a temperature less than the melting point of the crowns, and the heating of the crowns causes the flux to begin to flow at about 1000° Fahrenheit and subsequently boil to provide a caustic action to cleanse oxides from the metal surfaces. This is easily accomplished using the present invention since the crown alloy has a melting point of approximately 2150° Fahrenheit.

When the necessary deoxidation of the surfaces of the crowns has occurred, an acceptable solder for the alloy is applied in a perform. For example, The J. M. Ney Company OPTION pre-porcelain Solder, Catalog No. 392-13-11, which melts in the range of 1866°–1947° Fahrenheit may be used. Thus, after the fluxing of the alloy crowns, the solder performs may be placed therebetween and the power level of the infra-red lamp selected to be sixty to eighty percent of full power to subject the solder to a lower temperature than the melting point of the crown alloy. Thereafter, when the solder perform is melted and bonds to the two crowns, a two-unit bridge is formed and ready to be porcelainized.

Porcelainizing is accomplished by coating the crowns with the porcelain in a semi-liquid form and thereafter subjecting the coated bridge to the heating operating to fire the porcelain to produce the porcelain coating thereon.

The invention further provides an advantage in that, after porcelainizing of the crown or bridge, and after the dentist has checked the crown or bridge for the proper bite of the dental patient, the dentist may slightly grind the porcelainized bridge and then subject the ground portion of the crown to sufficient heat to create a glaze over the ground portion(s) of the porcelain coating.

Using the present invention, dental techniques in the forming and filling of bridges for patients is greatly simplified and the potential for thermal distortion is minimized.

Figure 5:
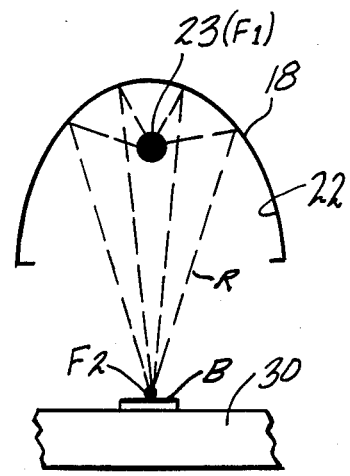
FIG. 5 is a schematic diagram exemplifying the operation of the device of FIG. 1.

FIG. 5 exemplifies the infra-red energy R reflected from the surface 22 of the reflector 18. The lamp 23 is shown at a first focal point F1 of the elliptical reflector. The reflected energy is concentrated at a small area shown as focal point F2. In FIG. 5, a thermal insulating block B is shown on the platform 30. The workpiece to be heated is placed on block B. Previously, the probe 42 had been used to bring the platform 30, the block B and the workpiece thereon to focal point F2.

Although the invention has been described primarily for use in the dental area, it may also be used in any environment in which precise heating is required, for example, in soldering components to printed circuit boards where localized and controlled values of applied heat are required.

It may thus be seen that the objects of the invention set forth, as well as those made apparent from the foregoing description, are efficiently attained. Although a preferred embodiment of the invention has been set forth for purposes of disclosure, modifications to the disclosed embodiment of the invention, as well as other embodiments thereof, may occur to those skilled in the art. Accordingly, the appended claims are intended to cover all embodiments of the invention and modifications to the disclosed embodiment which do not depart from the spirit and scope of the invention.

Having thus disclosed the invention, what is claimed is:

1. Apparatus for heating a workpiece to a predetermined temperature comprising a reflector having an axis with first and second focal points therealong; a source of radiant energy axially located substantially at first focal point within said reflector whereby said reflector reflects energy from said source to said second focal point; housing means supporting said reflector and source; a support assembly; means mounting said housing means on said support assembly in a fixed position; a platform movably supported on said support assembly below said housing for reciprocal movement along a vertical axis relative to said second focal point; means for vertically moving said platform on said support assembly relative to said housing along said vertical axis; a vertically extending probe member; an arm having one end pivotally mounted on said support assembly for pivotal movement in a plane normal to said vertical axis and carrying said probe member adjacent its other end, said probe member depending from said arm and having a free lower end locatable in a plane which essentially includes said second focal point, said arm being pivotable to move the free end of said probe member to a position in which it extends coaxially of said reflector and the free end of said probe member indicates said second focal point and to a second position wherein said arm and probe member are disposed outwardly of the radiant energy reflected from said reflector.

2. The apparatus of claim 1 wherein said source of energy is electrically excited, and wherein there is included means for exciting said source at a predetermined different number of power levels to predetermine the heat energy applied to a workpiece at sais second focal point.

3. The apparatus of claim 2 further including means for varying the electrical power applied to said source between succeeding power levels.

4. In a method for heating a workpiece to a predetermined temperature, the steps comprising:
   (a) providing a housing, an elliptical reflector supported in a fixed position on said housing and having a central axis, and a source of infra-red energy within said reflector along said axis essentially at a first focal point therewithin so that energy from said source is reflected to a second focal point along said axis outside of said reflector;
   (b) providing an arm having one end pivotally mounted on said housing for pivotal movement in a plane normal to said vertical axis and carrying said probe member adjacent its other end, said probe member depending from said arm and having a free lower end disposable in a plane including said second focal point along said axis of said reflector;
   (c) providing a vertically movable platform on said housing beneath said reflector;
   (d) placing a workpiece to be heated on said platform;
   (e) moving said probe member so that said free lower end of said probe is coaxial with said axis of said reflector and lies in said plane of said second focal point;
   (f) vertically moving said platform upwardly on said housing relative to said reflector to position said workpiece essentially at said lower free end of said probe member;
   (g) pivoting said arm about its pivotal axis to move said probe member to a second position outwardly of the path of said energy reflected by said reflector; and
   (h) electrically energizing said source at a predetermined energy level for a selected time to heat said workpiece.

5. The method for heating a workpiece in accordance with claim 4 wherein said workpiece comprises a pair of crowns of dental alloy spaced a limited, predetermined distance apart; wherein a flux is applied between said crowns; wherein said crowns are subjected to localized infra-red energy to heat said crowns to a temperature which is sufficient to cause said flux to liquify and clean adjacent surfaces of said crowns but insufficient to melt said crowns; wherein solder is placed between said crowns; and wherein said solder is subjected to infrared energy to generate a temperature sufficient to melt said solder and cause it to adhere to and join said crowns, but below the melting temperature of the alloy of said crowns.

6. The method for heating a workpiece in accordance with claim 5, further including the step of porcelainizing said bridge after said crowns are soldered together.

* * * * *